United States Patent [19]
Bowley

[11] 3,960,657
[45] June 1, 1976

[54] METHOD FOR OXYGENATING BLOOD

[75] Inventor: Wallace W. Bowley, Stafford Springs, Conn.

[73] Assignee: Intech, Inc., Manchester, Conn.

[22] Filed: July 24, 1975

[21] Appl. No.: 598,630

Related U.S. Application Data

[62] Division of Ser. No. 295,724, Oct. 6, 1972, Pat. No. 3,898,045.

[52] U.S. Cl. ............................ 195/1.8; 23/258.5 A; 23/258.5 BH
[51] Int. Cl.² ....................................... A61M 1/03
[58] Field of Search...... 261/122, DIG. 26, DIG. 28; 55/255, 256; 195/1.8; 128/DIG. 3; 23/258.5 R, 258.5 A, 258.5 B, 258.5 BH, 258.5 M, 258.5 MH

[56] References Cited
UNITED STATES PATENTS

| | | | |
|---|---|---|---|
| 2,934,067 | 4/1960 | Calvin | 23/258.5 |
| 3,175,555 | 3/1965 | Ling | 23/258.5 |
| 3,204,631 | 9/1965 | Fields | 23/258.5 |
| 3,291,568 | 12/1966 | Sautter | 23/258.5 |
| 3,468,631 | 9/1969 | Raible et al. | 23/258.5 |
| 3,488,158 | 1/1970 | Bentley et al. | 23/258.5 |
| 3,513,845 | 5/1970 | Chesnut et al. | 23/258.5 |
| 3,547,591 | 12/1970 | Torres | 23/258.5 |
| 3,578,411 | 5/1971 | Bentley et al. | 23/258.5 |
| 3,729,377 | 4/1973 | Leonard | 23/258.5 |
| 3,769,162 | 10/1973 | Brumfield | 23/258.5 |

FOREIGN PATENTS OR APPLICATIONS

| | | | |
|---|---|---|---|
| 1,089,125 | 9/1960 | Germany | 23/258.5 |
| 302,125 | 6/1971 | U.S.S.R. | 23/258.5 |

Primary Examiner—Morris O. Wolk
Assistant Examiner—Bradley Garris
Attorney, Agent, or Firm—Weingarten, Maxham & Schurgin

[57] ABSTRACT

A method for oxygenating blood by combining blood and oxygen in a receptacle to form a foam, the foam flowing upwardly through a bead bed having a multitude of tortuous paths and contact surfaces. The oxygenated blood is then defoamed and collected for recirculation to the patient.

6 Claims, 3 Drawing Figures

METHOD FOR OXYGENATING BLOOD

CROSS REFERENCES TO RELATED APPLICATIONS

This is a division of application Ser. No. 295,724, filed Oct. 6, 1972, and now U.S. Pat. No. 3,898,045.

FIELD OF THE INVENTION

This invention relates to blood oxygenators and more particularly concerns a simple, relatively inexpensive, disposable blood oxygenator and heat exchanger which can be used as a substitute for the lungs of an animal or human being during surgery.

DISCUSSION OF THE PRIOR ART

Many devices have been developed for purposes of oxygenating a patient's blood during cardiac or related surgery. Both bubble type and film type oxygenators are known. The older film type devices in which the oxygen must pass through a semi-permeable membrane into the blood are characterized by a very slow rate of oxygenation. The bubble type oxygenators allow for direct mixing of oxygen bubbles with the oxygen depleted blood. However, using a sufficient oxygen-blood ratio to produce an acceptable oxygen diffusion rate in such a device tends to create turbulence which causes trauma in the blood cells resulting in hemolysis, a physical breakdown of the blood cells themselves. It is evident that for patient safety, hemolysis must be kept to a minimum.

In bubble type oxygenators there is a relationship between bubble surface area and film resistance to diffusion which should be optimized in order to maximize the diffusion rate. For a given gas flow rate a small number of large bubbles has too small a mass transfer area for efficient diffusion, whereas a large number of very small bubbles has sufficient interface area but inefficient diffusion characteristics. As might be expected, there exists an optimum size bubble for most efficient diffusion. Certain well known physical properties have a bearing upon diffusion rate, an important one being surface film resistance. At the surface of each oxygen bubble there exists a layer of oxygen saturated blood. This is an effective boundary layer which reduces the rate at which the remainder of the oxygen bubble diffuses into the blood thereby reducing the overall oxygenation rate for a given gas flow rate. This boundary layer is more effective for reducing diffusion of small bubbles than of large bubbles. Diffusion rate also relates to the speed at which bubbles rise through the blood. It may thus be appreciated that attempts have been made to produce bubbles of relatively precise size in prior bubble type oxygenators. This gives rise to the present necessity of manufacturing the oxygen bubble diffuser to very close tolerances, a difficult and expensive task at best.

Apparatus has also been devised where the diffusion chamber is filled with spherical bodies in order to provide a sufficient agitation for enhanced oxygenation (Russian Pat. No. 302,125). In that device the blood is made to flow in one direction and the oxygen in the opposite direction through the oxygenator for the stated reason of increasing the rate of diffusion. However, turbulence will likely occur when the oxygen and the blood travel in opposite directions and a significant amount of hemolysis may thereby result. That invention does not provide a means for preventing hemolysis due to the movement or vibration of the spherical bodies in the chamber as the oxygen and blood move through, nor does it provide for a means to control bubble size. Further, due to the substantial resistance to blood flow caused by the opposite direction oxygen flow it would be necessary to pump the blood through the device, effectively sucking the blood from the patient. The dangers inherent in this practice are obvious. The increased resistance to blood flow tends to further reduce the efficiency and speed of operation of the Russian oxygenator.

In order to prevent injury to the patient, it is necessary that the blood returned to the arteries be entirely free of any gas bubbles. It is therefore necessary that the bubble-type oxygenators have additional provisions for defoaming the blood after it has been oxygenated because at that point the blood is in the form of a foam. Several previous devices employ a cylinder packed with chips or fibers soaked in a conventional chemical defoaming or non-wetting agent to break down the bubbles. These structures do not have a uniform density defoamer so that defoaming action is different at different locations within the defoamer. Serious danger to the patient has resulted from this type of defoamer for two primary reasons. Excess defoaming agent has been known to have entered the blood, thus contaminating it and causing permanent brain damage to patients. Also the defoaming agent in the defoamer eventually becomes exhausted and defoaming action decreases with time until it is too slow to be useful. Proposed methods of time-regulated discharge of the defoaming agent are complicated and are not sufficiently reliable. The difficulties associated with the process of defoaming severly limit the rate of blood flow through many of the presently known oxygenators.

The devices of the prior art tend to have a limited flow rate efficiency. Present applications of these devices in cardiac and related surgery indicate that an improvement in blood flow rate and oxygenation efficiency as well as reliability in defoaming would be of great benefit to the medical profession and to patients.

SUMMARY OF THE INVENTION

Generally speaking, the invention herein disclosed is an improved blood oxygenator for use as a substitute for the lungs of a patient during cardiac and related surgery. It comprises a diffuser from which oxygen bubbles of relatively uniform predetermined size flow into an ejector filled with blood to make a mixture of blood and oxygen. This mixture flows through a chamber filled with spherical hard beads of uniform size forming a lattice structure. As the oxygen bubbles and the blood move through the bead lattice, oxygen is diffused into the blood and carbon dioxide is removed therefrom. This reaction is facilitated by frictional contact between the beads and the bubbles in the blood as they pass through the bead lattice. The resulting action may properly be termed a "wiped film" bubble oxygenation process. The oxygenated blood foam thus generated leaves the lattice chamber and enters a defoaming section which has radially and axially uniform defoaming properties. Several defoamer embodiments are set forth in the detailed description hereinbelow. The oxygenated defoamed blood flows over a heat exchanger in order to effect whatever temperature changes are desired and from there it flows into a calibrated blood reservoir, ready to return to the arterial system of the patient.

The object of this invention is to provide a simple, relatively inexpensive, disposable blood oxygenator having significantly improved blood flow rate and oxygenation efficiency. Additionally, this oxygenator includes a reliable and constant defoamer which substantially reduces the possibility of dangerous contamination of the blood by chemical anti-foaming agents.

BRIEF DESCRIPTION OF THE DRAWINGS

The objects, advantages and features of this invention will become readily apparent from the following detailed description when taken in conjunction with the accompanying drawing, in which.

DETAILED DESCRIPTION OF THE INVENTION

Figure 1:
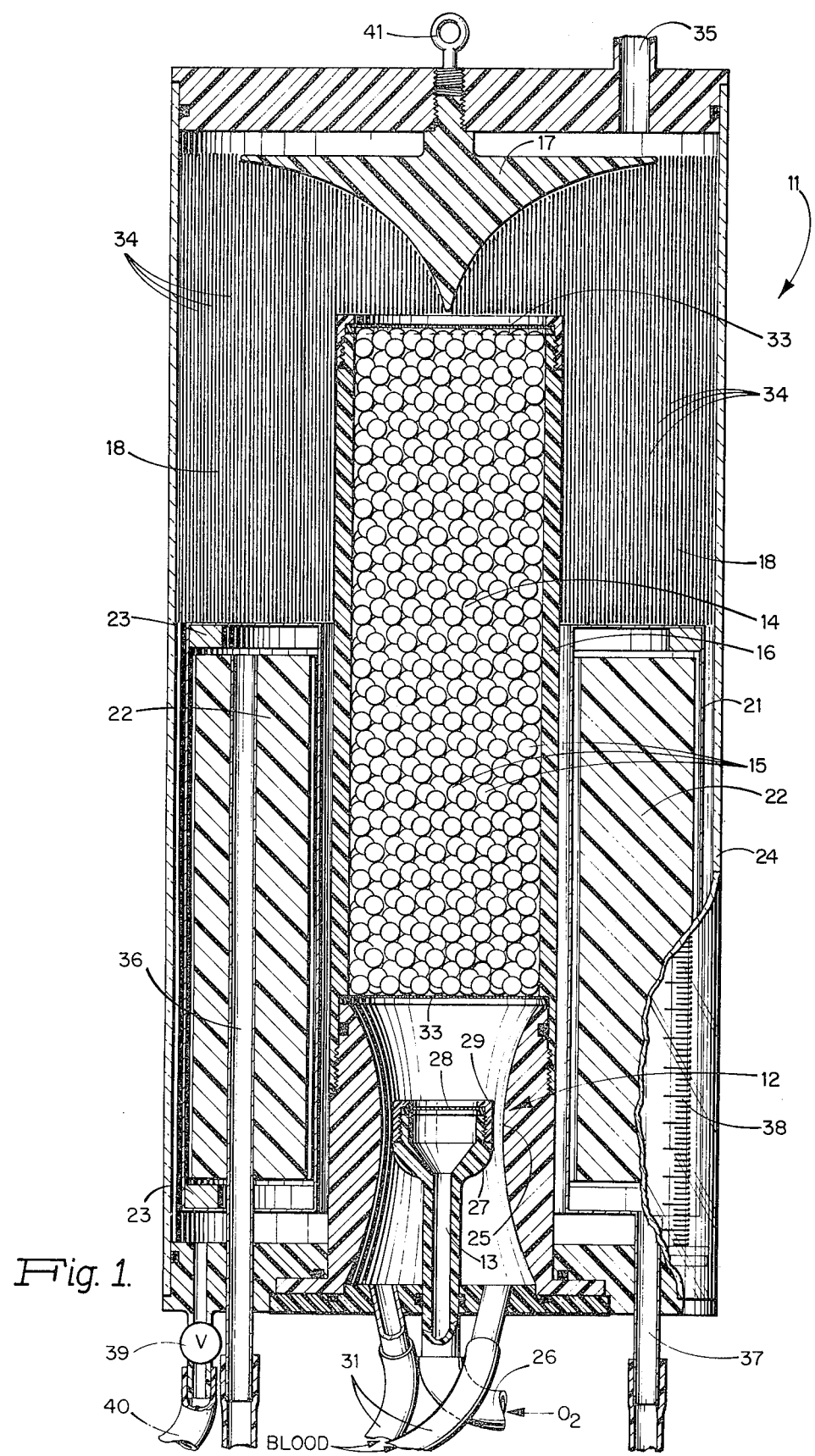
FIG. 1 is a sectional view of an oxygenator constructed in accordance with this invention.

With reference now to the drawing there is shown an oxygenator 11, preferably of cylindrical configuration, which comprises ejector 12, a diffuser 13 within the ejector, a lattice chamber 14 formed of a bed of rigid beads 15 in a cylinder 16, a diverter 17, a defoamer 18, a heat exchanger 21 having a core 22 supported by rings 23 therein, and a graduated reservoir 24.

Figure 2:
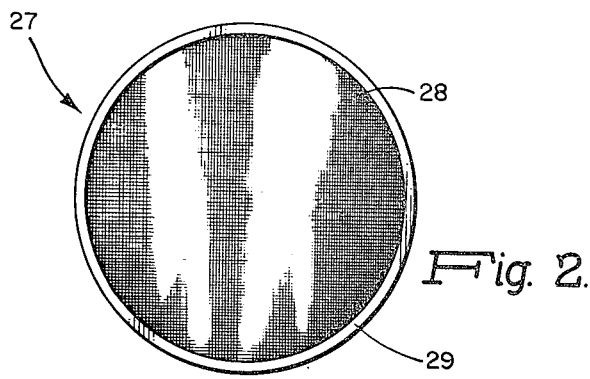
FIG. 2 is a top view of the diffuser head shown as part of the blood oxygenator of FIG. 1.

Ejector 12 is essentially a mixing chamber and bubble pump having side walls 25 which are concave inward. Oxygen is supplied through conduit 26 to the oxygenator from an outside source (not shown), entering diffuser 13. Diffuser head 27, shown in detail in FIG. 2, is constructed of a close weave fabric 28 having openings of uniform size secured to a retaining ring 29 attached to the top of diffuser 13. The fabric may be Dacron (a registered trademark) or other suitable material having relatively uniform openings approximately forty microns across. Retaining ring 29 may be any non-corrosive relatively rigid material such as Lucite (a duPont trademark) or stainless steel. Since a relatively inexpensive, disposable yet sturdy structure is contemplated, a rigid plastic retaining ring is preferred. Of course, the oxygenator of this invention is not limited to being disposable and the materials used may vary due to different requirements of the users.

Referring again to FIG. 1, oxygen depleted venous blood enters the ejector through conduits 31. Note that there are two inputs which enter the bottom of the ejector at an angle in order to provide a gentle swirling motion. The ejector is normally full of blood and at the beginning of an operation must be primed with blood or a saline solution in the normal manner. Oxygen is released from diffuser head 27 forming bubbles of substantially uniform size in the blood. As will be seen later, the preciseness of bubble size is not critical. With the oxygen entering the blood at the location indicated at a relatively high velocity, the ejector with its concave walls 25 acts as a bubble pump. This structure not only moves the blood through the oxygenator, but effectively causes the oxygen bubbles to be mixed throughout the blood at the top of the ejector as the mixture enters the lattice chamber.

The beads in the lattice chamber are tightly packed and are of uniform size. These beads are preferably 6 mm in diameter but beads ranging from 3 mm to 10 mm may be used. The beads may be made of any suitable material which provide a relatively smooth, hard surface. While glass is the substance normally preferred, many other materials such as polyethylene and polytetrafluoroethylene may be used. The function of the lattice chamber will be discussed in detail hereinbelow. A coarse mesh cloth 33 separates the bead bed from the ejector and may be mounted to the bottom of cylinder 16 by a conventional retaining ring or other suitable means. Cloth 33 has a mesh opening sufficiently small so as to prevent any of the beads from escaping from the lattice chamber while permitting free flow of the blood/oxygen mixture from the ejector to the lattice chamber. The top of the lattice chamber is also fitted with a similar coarse mesh cloth 33 to prevent any of the beads from escaping into the defoamer.

It has been found that very little trauma is necessary to cause hemolysis, that is, injury to the blood cells. For this reason, the beads in the chamber are preferably secured together to prevent any vibration or movement within the lattice network. Ultrasonic welding is one good way of accomplishing this desired result. Even with the beads secured together, mesh elements 33 are employed at either end of the cylinder 16 in case one of the beads should come loose.

When oxygen bubbles are mixed with blood and diffusion begins to take place, a boundary layer of oxygen saturated blood is formed at the surface of each bubble. This boundary layer resists further diffusion of oxygen into the oxygen depleted blood lying beyond the layer. To help counteract this resistance to complete oxygenation, this invention teaches that the bubble is made to traverse a long and tortuous path through the bead lattice. As the bubble encounters each solid bead, there is a wiping action at the diffusion resistant boundary layer of the bubble which physically dislodges or breaks down the boundary layer and results in decreased resistance to the diffusion of oxygen into the blood. The boundary layer reforms as the bubble retreats from each collision with a bead but as each oxygen bubble makes its way upward through the bead lattice, it has a large number of collisions with beads. In the course of each collision, the boundary layer is temporarily broken down and diffusion is facilitated. The rate of diffusion of oxygen in the venous blood is increased by the presence of the beads because of the greatly increased surface area for diffusion which the beads provide and by the wiping effect produced by the bubblebead collisions. It may thus be appreciated that the terminology "wiped film bubble oxygenation process" is quite appropriate.

According to this invention, the flow of oxygen and venous blood is in the same upward direction through the center of the oxygenator, thus eliminating significant resistance to blood flow in opposite directions. In addition, the common directional flow of blood and oxygen bubbles means that blood and oxygen are in contact throughout the time that the blood is flowing through the lattice chamber, thus increasing the diffusion rate. Also, the co-directional flow of the blood and oxygen avoids the turbulence which would result from the collision of two oppositely directed flows.

According to the invention there are uniform size passageways between the beads 15 in the lattice chamber 14 because the beads themselves are uniform in size. These constricted passageways regulate to a very close tolerance the size of the oxygen bubbles which can pass through the bead lattice. It is well known in the art that in bubble type oxygenators there is a balance between bubble area and film resistance which is difficult to achieve as has previously been stated. It is necessary to maintain a balance in bubble size in order to maximize diffusion and this must be done accurately. In conventional bubble type oxygenators, this is attempted by means of a diffuser with openings manufactured to very close tolerances. In the present invention, the uniform spacings between the beads can be designed to permit only bubbles of the desired size to proceed through the bead lattice, thereby providing maximum diffusion efficiency. Larger bubbles will be separated as they pass through the restricted passageways between the beads, thereby accomplishing the desired effect. Consequently, fabric 28 on diffuser head 27 need not be manufactured to extremely close tolerances since the bead bed will reduce bubble size as the mixture passes through it.

It is now apparent that several factors of the present invention contribute to increased diffusion speed and efficiency. Among these factors are the cumulatively large surface area of the beads, the wiping action produced by contact between the pliable bubbles and the hard beads, the long mutual contact time resulting from co-directional flow of blood and oxygen and the long path of travel which results from the presence of the closely packed beads. Such factors enable the oxygenator of the present invention to be operated at a lower oxygen/blood flow ratio than is possible in conventional oxygenators. It is well known in the art that when the oxygen/blood flow ratio is decreased, the turbulence which occurs in the blood-oxygen mixture also decreases. When turbulence decreases, hemolysis is significantly reduced. Thus an important effect of the present invention is greatly reduced hemolysis, while maintaining an overall high diffusion efficiency.

The oxygenated blood foam contacts diverter 17 directly from the top of lattice chamber 14. The diverter consists of a concave conical surface preferably made of clear plastic although other shapes and materials may be used. The foam is directed outward by the diverter and enters defoamer 18 which surrounds the top portion of the lattice chamber above the heat exchanger. Note that the defoamer fabric extends to the center of the oxygenator between the top of the lattice chamber and the diverter.

Figure 3:
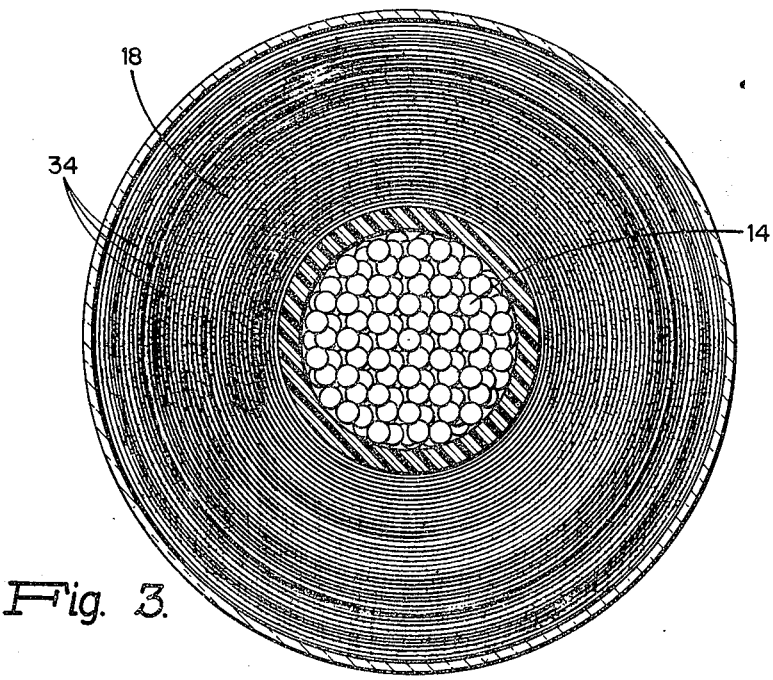
FIG. 3 is a top view showing the defoaming section of the oxygenator of FIG. 1.

With reference now to FIG. 3, a top view of defoamer 18 is shown. It consists of a woven cloth 34 which is wound around the upper portion of the lattice chamber a predetermined number of turns in order to insure radial uniformity and consistency in production. Defoaming may be achieved in the well-known manner wherein bubbles containing carbon dioxide and oxygen collapse on fibers which have been coated by spraying or dipping with a chemical anti-foam or non-wetting agent. A preferred embodiment of the defoamer is to wrap the lattice chamber with a material comprising two alternating layers of fabric, one wetting and one non-wetting. In this embodiment the bubbles are pulled apart by being repelled from the non-wetting material and attracted to the wetting material whereon it collapses and drains to the reservoir 24. An alternative preferred embodiment of the defoamer is to use a cloth woven of wetting fibers running horizontally and non-wetting fibers running vertically. The bubbles are repelled and attracted as stated above, causing the bubbles to collapse in a single vertical plane and drain to the reservoir. These two preferred embodiments utilize fibers whose wetting and non-wetting properties are inherent in the materials themselves rather than the result of treatment with chemical agents. Examples of non-wetting materials are nylon and polytetrafluoroethylene, while wetting materials may be glass fiber or fibers from the polycarbonate family such as Lexan (a registered trademark). These embodiments have the advantage of stability, that is the non-wetting and wetting properties of the fibers are constant in time. Further, there is no likelihood of dangerous contamination of the patient's blood with anti-foam agent. The cloth of the defoamer is wound relatively tightly around the lattice chamber so that each successive turn contacts the adjacent turns and there is radial uniformity from the lattice chamber outward to the wall of the oxygenator. The defoamer fills all of the space between cylinder 16 and the walls of the oxygenator which lies between the heat exchanger and the diverter.

Carbon dioxide and excess oxygen released from the blood as it is defoamed is exhausted from the oxygenator through vent 35 in the top of the defoamer. The vent may be equipped with a conventional bacteriological filter (not shown) to prevent possible contamination of the atmosphere in the operating room.

The oxygenated blood drains from the defoamer and is allowed to flow over the heat exchanger 21. The heat exchanger is an annular cylindrical container with an annular core 22 of closed cell foam filling the bulk of the interior thereof. The core is held in place by means of rings 23 at the top and bottom of the container. Heated or cooled water is pumped through the heat exchanger, entering through conduit 36 and leaving through conduit 37. The blood is thereby maintained at a predetermined desired temperature. Fluid other than water could be used if desied. This particular configuration for the heat exchanger permits a large surface area for rapid temperature adjustment of the blood flowing over its sides while having a reduced interior volume to permit rapid fluid exchange within it.

The oxygenated blood of desired temperature is stored in a reservoir 24 which preferably has transparent walls. The reservoir is an annular configuration and surrounds the ejector and diffuser and the lower end of the lattice chamber. The reservoir is calibrated (scale 38) as to volume in order that the amount of blood available can easily be monitored during the operation. The oxygenated blood is removed from the reservoir through tubing 40 controlled by conventional ball-type check valve 39 which closes the outlet when insufficient blood is present in the reservoir. This prevents any air from getting into the patient's arterial system in an emergency situation when the blood reservoir becomes empty. Note that the heat exchanger resides within the reservoir in order to maintain the blood temperature as desired.

A ring 41 is secured to the top of the oxygenator to provide for attachment of the unit to a ring stand holder. Preferably the main shell and most of the interior parts of this oxygenator are made of substantially rigid transparent plastic so that its proper operation may be observed at all times. The plastic elements may be secured together by adhesive or by other suitable means. By being made of plastic it is disposable, inexpensive to make and shatter resistant. The overall size of this oxygenator is approximatey 18 inches in height and 7 inches in diameter for adults. Because the volume necessary for babies is much less, a reduced size oxygenator is available for pediatric purposes. Of course, the size specified above is by way of example only and is in no way limiting.

The invention herein disclosed is a very compact, vertically hung oxygenator. Installation time and operator training are minimal since the device is pre-sterilized and disposable, while being very simple to set up and operate. Those skilled in the art will readily appreciate that various modifications and improvements to this oxygenator may be made to suit particular requirements which are within the scope of the invention.

What is claimed is:

1. A method for oxygenating blood employing an elongated lattice chamber having a multiplicity of immovable rounded surfaces disposed throughout its volume thereby creating a plurality of tortuous paths through said lattice chamber, said method comprising the steps of:
   flowing a supply of venous blood into a receptacle adjacent one end of said lattice chamber;
   introducing oxygen bubbles into the blood in said receptacle;
   mixing the blood and oxygen bubbles together to form a blood foam comprising bubbles formed of a blood surface surrounding a volume of oxygen;
   flowing the blood foam substantially unidirectionally through said lattice chamber whereby said blood surfaces of said blood foam bubbles collide with a multiplicity of said rounded surfaces in moving, frictional, wiping contact therewith, thereby resulting in the transfer of oxygen to said blood surfaces from the oxygen contained within said blood foam bubbles, whereby oxygenation of the venous blood is achieved; and
   breaking down the oxygenated blood foam into oxygenated fluid blood and gases.

2. The method for oxygenating blood according to claim 1 and further comprising the steps of:
   venting said gases from the vicinity of said oxygenated fluid blood; and
   collecting said oxygenated fluid blood.

3. The method for oxygenating blood according to claim 1 wherein said breaking down step includes the step of bringing said blood foam into simultaneous contact with a multiplicity of adjacent, alternately fluid attracting and fluid repelling fibers.

4. The method for oxygenating blood according to claim 1 wherein said step of introducing oxygen bubbles into said receptacle comprises the steps of:
   injecting said oxygen bubbles into said venous blood at a flow velocity greater than the flow velocity of the flow of said blood into said receptacle and in the same direction as said blood flow to form a mixture of blood and oxygen; and
   expanding said mixture of oxygen and venous blood to form a blood foam.

5. A method for oxygenating blood according to claim 1 and further comprising the steps of:
   adjusting the temperature of said oxygenated fluid blood; and
   measuring and storing a supply of said oxygenated fluid blood.

6. The method for oxygenating blood according to claim 1 and further comprising the step of spreading the bubbles of said blood foam substantially uniformly over the cross-section of the inlet end of said lattice chamber.

* * * * *